US008852526B2

(12) United States Patent
Shen et al.

(10) Patent No.: US 8,852,526 B2
(45) Date of Patent: Oct. 7, 2014

(54) METHOD OF FABRICATING MICROFLUIDIC SYSTEMS

(75) Inventors: Wei Shen, Victoria (AU); Xu Li, Victoria (AU); Junfei Tian, Melbourne (AU); Mohidus Samad Khan, Dhana (BD); Gil Garnier, Frankston (AU)

(73) Assignee: Monash University, Clayton (AU)

( * ) Notice: Subject to any disclaimer, the term of this patent is extended or adjusted under 35 U.S.C. 154(b) by 0 days.

(21) Appl. No.: 13/003,647

(22) PCT Filed: Jul. 10, 2009

(86) PCT No.: PCT/AU2009/000889

§ 371 (c)(1), (2), (4) Date: Jun. 13, 2011

(87) PCT Pub. No.: WO2010/003188

PCT Pub. Date: Jan. 14, 2010

(65) Prior Publication Data

US 2012/0009662 A1 Jan. 12, 2012

(30) Foreign Application Priority Data

Jul. 11, 2008 (AU) ................................ 2008903553
Nov. 7, 2008 (AU) ................................ 2008905776

(51) Int. Cl.

| | |
|---|---|
| ***G01N 15/06*** | (2006.01) |
| ***G01N 33/00*** | (2006.01) |
| ***G01N 33/48*** | (2006.01) |
| ***D21H 21/16*** | (2006.01) |
| ***D21H 17/17*** | (2006.01) |
| ***D21H 17/16*** | (2006.01) |
| ***D21H 19/10*** | (2006.01) |
| ***B01L 3/00*** | (2006.01) |

(52) U.S. Cl.

CPC ............... *D21H 17/17* (2013.01); *D21H 21/16* (2013.01); *D21H 17/16* (2013.01); *B01L 2300/161* (2013.01); *B01L 2300/126* (2013.01); *B01L 2200/12* (2013.01); *B01L 2200/10* (2013.01); *D21H 19/10* (2013.01); *B01L 3/502707* (2013.01)

USPC .......... 422/503; 422/68.1; 422/502; 422/507; 436/43

(58) Field of Classification Search

USPC ................................ 422/68.1, 502, 503, 507

See application file for complete search history.

(56) References Cited

U.S. PATENT DOCUMENTS 5,904,824 A 5/1999 Oh
6,518,168 B1 2/2003 Clem et al.

(Continued)

FOREIGN PATENT DOCUMENTS

WO WO 2006074665 7/2006
WO WO 2008060449 5/2008

OTHER PUBLICATIONS

Abe et al., "Inkjet-printed microfluidic multianalyte chemical sensing paper", Analytical Chemistry, Sep. 2008, 6928-6934.

Bruzewicz et al., "Low-cost printing of poly(dimethylsiloxane) barriers to define microchannels in paper", Analytical Chemistry 80, May 2008, 3387-3392.

Martinez et al., "Flash: A rapid method for prototyping paper-based microfluidic devices", Lab on a Chip, Aug. 2008, 8, 2146.

(Continued)

*Primary Examiner* — Brian J Sines

(74) *Attorney, Agent, or Firm* — Baker & Hostetler LLP

(57) ABSTRACT

A method of fabricating a microfluidic system having microfluidic channels on a surface of a hydrophilic substrate, the method including the steps of: hydrophobizing the substrate surface; locating a mask defining the substrate surface, the mask having open areas defining the periphery of the microfluidic channels; and applying an irradiation treatment to areas of the substrate surface exposed by the open areas of the mask, said exposed areas becoming hydrophilic to therefore form said microfluidic channels.

10 Claims, 5 Drawing Sheets

(56) References Cited

U.S. PATENT DOCUMENTS

| | | | | |
|---|---|---|---|---|
| 7,125,639 | B2 | 10/2006 | Schaper | |
| 2004/0242794 | A1 * | 12/2004 | Kanazawa | 525/327.3 |
| 2007/0137812 | A1 * | 6/2007 | Shannon et al. | 162/109 |

OTHER PUBLICATIONS

Martinez et al., "Patterned paper as a platform for inexpensive, low-volume, portable bioassays", Angew. Chem. Int. Ed., 2007, 46, 1318-1320.

* cited by examiner

METHOD OF FABRICATING MICROFLUIDIC SYSTEMS

CROSS-REFERENCE TO RELATED APPLICATIONS

This application is the National Stage of International Application No. PCT/AU2009/000889 filed Jul. 10, 2009, which claims the benefit of Australian Application No. 2008903553, filed Jul. 11, 2008, and Australian Application No. 2008905776, filed Nov. 7, 2008, the disclosures of which are incorporated herein by reference in their entireties.

TECHNICAL FIELD

The present invention is generally directed to microfluidic systems, and fabrication of such systems on low cost substrates such as paper, woven fabric and non-woven cellulosic material.

BACKGROUND TO THE INVENTION

The concept of making inexpensive microfluidic channels on paper and other woven and non-woven fibrous and porous surfaces has been successfully proven. The aim of building such systems has been to fabricate low-cost bio-analytical and indicator devices, with direct envisaged applications in detecting waterborne bacteria and metals ions in drinking water, the presence of some specific proteins or biomarkers in body fluid (cancer test), the level of glucose and other biochemical substances in human or animal blood and urine samples. Developments of low-cost paper-based bio-analytical and environmental analytical devices have so far allowed quick and single step reaction to detect analytes in a fluid sample.

Researchers in Harvard University led by Whitesides (see Martinez, A. W., Phillips, S. T., Butte, M. J. and Whitesides G. M., and "Patterned Paper as a platform for Inexpensive, Low-Volume, Portable Bioassays", Angew. Chem. Int. Ed. 46, 1318-1320 (2007)) have recently created channels on paper by printing patterns of conventional photoresists polymers (PMMA). Paper provides the capillary channels, while the photoresist polymers form the barrier which defines the channel. More recently, the Harvard group further developed their photoresist technique in making fine channels in paper. They used an ink jet printer to print patterns on transparent polymer films, which were used as masks for photo lithography to generate photoresist patterns in paper following their published approach (Martinez, A. W., Phillips, S. T., Wiley, B. J., Gupta, M. and Whitesides, G. M. Lab on a Chip, (2008) DOI: 10.1039/b811135a). They showed that fine microfluidic channels can be generated in paper using the photoresist barrier approach and these channels have comparable resolution to the microfluidic channels made using other substrates such as silicon wafer. A problem associated with the use of such photolithography techniques is that they result in rigid and brittle barriers which can be easily damaged if the paper is creased or crumpled.

In another published paper, the Harvard group used an x-y plotter to draw channels on paper surface (see Bruzewicz, D. A., Reches, M. and Whitesides, G. M., "Low-Cost Printing of Poly(dimethylsiloxane) Barriers to Define Microchannels in Paper", Anal Chem. 80, 3387-3392 (2008)). The plotter's pens were filled with a hydrophobic solution of polydimethyl siloxane (PDMS) in hexane, and a plethora of patterns several centimeters long with channel 1 cm to 2 mm wide were created. Their second micro-channels system created on paper surface overcame a major drawback of the first one, ie the rigid and brittle barrier material of conventional photoresist polymers. Their second system, however, has a poor channel resolution and definition, since the penetration of PDMS solution in paper sheet cannot be controlled. The use of silicones to define the walls of the microchannels would also require FDA approval in view of the potential health related issues. Both fabrication approaches result in physical barriers which define the periphery of the micro-channels.

Abe et al. (Abe, K; Suzuki, K; Citterio, D. "Inkjet-printed microfluidic multianalyte chemical sensing paper", Anal. Chem. (2008) 6928-6934) presented a method of using a solution of hydrophobic polymer (PS) to impregnate paper. After the polymer physically covered the fibre surface and dried, they used a Microdrop dispensing device to deliver solvent droplets to dissolve the polymer from the fibre surface, thus forming microfluidic channels by restoring the hydrophilicity of the paper. These authors also used the Microdrop dispensing device to deliver chemical sensing agents into their pattern to form a functional device for biomedical detection.

In U.S. Pat. No. 7,125,639, Molecular Transfer lithography, the inventor Charles Daniel Schaper (class 430/253, 430/258) describes a process for patterning a substrate comprising the steps of: 1) coating a carrier with a photosensitive material, 2) exposing the photosensitive material to a pattern of radiation, and 3) physically transferring the exposed material to the substrate.

In U.S. Pat. No. 6,518,168, Self-assembled monolayers direct patterning of surfaces, by Paul G Clem et al (filing date Nov. 2, 1998), A technique for creating patterns of material deposited on a surface involves forming a self-assembled monolayer in a pattern on the surface and depositing, via chemical vapor deposition or via sol-gel processing, a material on the surface in a pattern complementary to the self-assembled monolayer pattern. The material can be a metal, metal oxide, or the like.

In WO/2008/060449 MICROFLUIDIC DETECTOR, by BUTTE, Manish, J. et al (Application date Sep. 11, 2007), articles and methods for determining an analyte indicative of a disease condition are provided. In some embodiments, articles and methods described herein can be used for determining a presence, qualitatively or quantitatively, of a component, such as a particular type of cell, in a fluid sample. In one particular embodiment, a low-cost microfluidic system for rapid detection of T cells is provided. The microfluidic system may use immobilized antibodies and adhesion molecules in a channel to capture T cells from a fluid sample such as a small volume of blood. The captured T cells may be labelled with a metal colloid (eg, gold nanoparticles) using an antibody specific for the T Cell Receptor (TCR), and metallic silver can be catalytically precipitated onto the cells. The number of T cells captured can be counted and may indicate a disease condition of a patient such as severe combined immune deficiency or human immunodeficiency virus.

Those patent applications and research papers proposed methods to make microfluidic systems and devices using a variety of materials, including using paper and other non-woven or porous materials as substrates. Microfluidic channels can be fabricated using paper and other non-woven or porous materials in batch operations. However all of the above-noted systems utilise complex and time consuming processes that cannot be readily adapted to allow for low cost, high speed industrial production. Furthermore, all these earlier systems rely on a physical barrier to define the microfluidic channels.

It is an object of the present invention to provide a method of fabricating a microfluidic system which overcomes at least one of the disadvantages of prior art methods.

SUMMARY OF THE INVENTION

With this in mind, according to one aspect of the present invention, there is provided a method of fabricating a microfluidic system having microfluidic channels on a surface of a hydrophilic substrate, the method including the steps of:

a) hydrophobizing the substrate surface;

b) locating a mask defining the substrate surface, the mask having open areas defining the periphery of the microfluidic channels; and c) applying an irradiation treatment to areas of the substrate surface exposed by the open areas of the mask, said exposed areas becoming hydrophilic to therefore form said microfluidic channels.

According to another aspect of the present invention, there is provided a microfluidic system fabricated according to the above described method.

The method according to the present invention provides a hydrophilic hydrophobic contrast within the substrate. This allows the substrate material to retain its original flexibility, unlike the prior art methods which utilise a physical barrier.

The hydrophilic substrate may be provided by a cellulosic material including paper, woven fabric and non-woven materials. The paper products can include filter paper, office paper, chromatography paper, tissues (towel, facial, bath wipes), newspaper, packaging paper, specialty papers, and so on. The preferential alignment of the fibres of the paper can be controlled or aligned using any technique known in the art. The paper can be surface treated with any of the usual techniques involving coating, surface sizing, spraying and the like.

The hydrophilic treatment acts to reduce the surface energy of the substrate surface. Various methods can be selected to hydrophobize the surface/substrate. An embodiment of the invention consists of absorbing or adsorbing a solution of hydrophobic substance dissolved in a volatile solvent. Hydrophobic substance include, but are not restricted to, alkyl ketene dimer (AKD), alkenyl succinic anhydride (ASA), rosin, latex, silicones, fluorochemicals, polyolefin emulsions, resin and fatty acids, natural and synthetic waxes and any hydrophobic substance known in the art. Another application is through vapour deposition of a hydrophobic substance.

The irradiation treatment acts to significantly increase the surface energy of the substrate surface rendering the treated areas with greater wettability by water and aqueous liquids. The wettability of the porous material by liquids then provides capillary driving force and allows the penetration of liquids within and along the channels created by the irradiation treatment.

The irradiation treatment may include plasma, corona and other irradiation treatments.

The microfluidic channels may preferably be in a pattern transporting a fluid to analyse in parallel to different detection zones. The typical channel dimensions vary in length from 10 cm to 1 mm and in width from 2 cm to 100 μm. The fluidic system has typically the same rigidity, mechanical, properties and softness as those of the original substrate.

It would also be advantageous to fabricate microfluidic systems using high volume, high speed and continuous printing methods which are able to provide on-demand microfluidic channel pattern variations.

With this in mind, according to a further aspect of the present invention, there is provided a method of fabricating a microfluidic system having microfluidic channels on a surface of a hydrophilic substrate, the method including the step of printing a hydrophobic agent on the substrate surface to thereby provide a hydrophobic/hydrophilic contrast thereon to define a peripheral edge of the microfluidic channels.

According to yet another aspect of the present invention, there is provided a microfluidic system fabricated according to the above described method.

The printing of the hydrophobic agent provides a hydrophobic/hydrophilic contrast between the peripheral edge of the microfluidic channels and the channels themselves. This is distinguished from prior art printing methods that seek to provide a physical barrier along the peripheral edge of the microfluidic channels.

The advantages of the present invention are the low manufacturing cost, the high processing speed and the exceptional pattern accuracy achievable. In one form of the invention a hydrophobic chemical (wax, polymer, oligomer or molecule) is dissolved in an organic solvent and printed. In another, a stable aqueous emulsion of the hydrophobic chemical is printed. The printed substrate can further be activated to fully develop the hydrophobicity via molecular rearrangement including the creation of covalent bonds. Of special interest are the hydrophobic materials used in the paper industry such as the internal sizing agents (AKD, ASA, rosin) and the surface sizing agents (polymers, latex). Our invention offers, for the first time, the possibility to manufacture at high speed, low cost and high quality micro-fluidic systems.

A possible manufacturing arrangement includes: 1) an unwinder, 2) a first printing station for the hydrophobic barrier, 3) an infra-red oven, (to activate) and 4) a rewinder, all arranged in series. Optional are 5) a cooling unit and 6) a second printing unit printing for the active system (biomolecule, reactive system). Should digital printers be selected (inkjet printers), on-demand pattern variations can be achieved. The invention is ideally suited to manufacture paper based diagnostic devices for health or environment analysis and control. The complete fluidic can be manufactured by printing, using a single line or even a single printer.

An ink may be formed with the hydrophobizing agent. A first option is to dissolve the hydrophobizing agent in an organic solvent for printing using common technology. A second option is to emulsify the hydrophobic agent into a stable aqueous ink. The advantage of this later option is that no volatile organic compounds (VOC) are emitted. VOC are to avoid under manufacturing conditions because of their important health and fire hazards.

After printing, the hydrophobic pattern can further be activated to fully develop the hydrophobicity via molecular rearrangement including the creation of covalent bonds. This is achieved by aging, heat, reaction or radiation. This treatment will also improve the permanency of the pattern.

While all hydrophobic compounds can be used as ink, the internal and surface sizing agents common in the Paper industry are especially attractive for their effectiveness, low cost, and low toxicity. Further they fulfil many health and safety requirements. Of special interest are alkyl ketene dimmers (AKD), alkenyl succinic anhydride (ASA), rosin, and the latex and polymers used in surface sizing The printing fluids can be printed on paper to fabricate microfluidic systems and devices using contact and non-contact printing processes and equipments, such as gravure, flexography, screen printing, ink jet printing, etc. In this application the applicants used digital ink jet printing to demonstrate the fabrication of microfluidic systems on paper.

Compared with the previous physical barrier fabrication methods, the new fabrication method according to the present invention enables the manufacturing of paper-based microfluidic devices in commercial scales and at low cost. Creation of hydrophilic-hydrophobic contrast is a simpler approach to define liquid penetration channels in paper than the physical barrier approach.

The use of digital printing technology to selectively deliver cellulose hydrophobization chemicals on paper surface to form the hydrophilic-hydrophobic contrast has some other advantages. Digital printing offers electronic pattern variation which allows fast change over for fabrication of different devices. Since the hydrophilic-hydrophobic contrast fabrication concept can retain the original flexibility of the paper, it offers natural bending and folding resistance, which fundamentally overcomes the poor bending and folding resistance often encountered with devices fabricated with other methods. These attributes are particularly attractive for personal care device applications such as in a diaper indicator application for example.

BRIEF DESCRIPTION OF THE DRAWINGS

It will be convenient to further describe the invention with respect to the accompanying drawings which illustrate preferred embodiments of the microfluidic system according to the present invention. Other embodiments of the invention are possible, and consequently, the particularity of the accompanying drawings is not to be understood as superseding the description of the invention.

In the drawings.

DETAILED DESCRIPTION OF THE INVENTION

The invention will now be described with reference to the following Examples describing different possible utilisations of the present invention. It is however to be appreciated that the invention is not restricted to these examples.

Example 1

Figure 1:
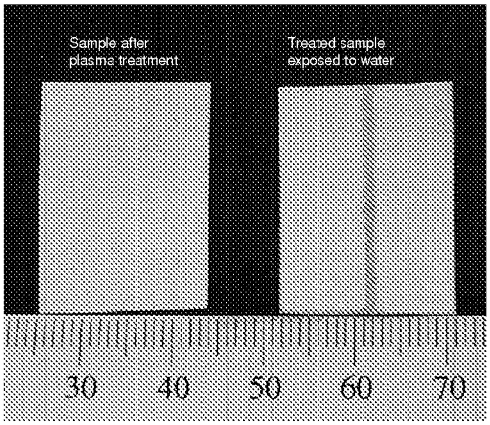
FIG. 1 shows a single microfluidic channel fabricated according to a first embodiment of the invention.

In one embodiment of the invention as shown in FIG. 1, a filter paper was hydrophobized by immersion in a solution of AKD dissolved in heptane and the solvent was allowed to evaporate. A heat treatment of the treated paper in an oven at 100° C. for 30-50 minutes was applied. In the second step, a solid mask was applied to the paper substrate and the system was exposed to a plasma reactor (K1050X plasma asher (Quorum Emitech, UK) for 10-100 seconds at the intensity of 12-50 W). The plasma treatment left no visible mark on the sample and the sample retained its original softness and flexibility. The treated channel becomes wettable by aqueous solutions and allows the capillary transport of the solutions. The width of the channel can be well controlled. FIG. 1 shows a single channel treated with a mask of 1 mm in width on filter paper, and shows the channel before and after wetting by water.

Figure 2:
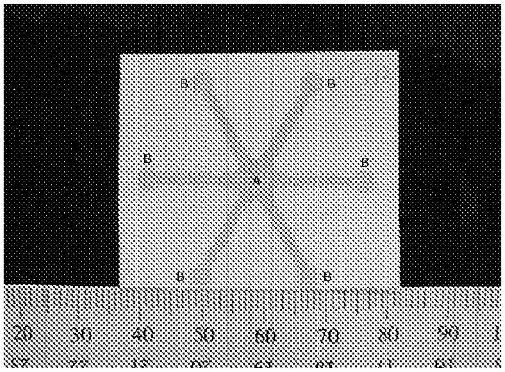
FIG. 2 shows a capillary channel pattern on filter paper fabricated according to the first embodiment of the invention.

The treated channel can have any geometrical pattern as shown in FIG. 2. First, a pattern includes a sample dosing zone (A) and one or multiple channels that lead to detection or reaction wells (B). Second, a pattern includes one or multiple sample dosing zones that are connected to one or multiple detection or reaction wells. In this example, a pattern of one sample dosing zone connected to multiple detection/reaction zones via capillary channels was created by plasma treatment.

A few drops of water were added to the sample dosing zone and the water was rapidly and accurately delivered to all detection/reaction wells where indicators were to be added as shown in FIG. 2.

Example 2

Figure 3:
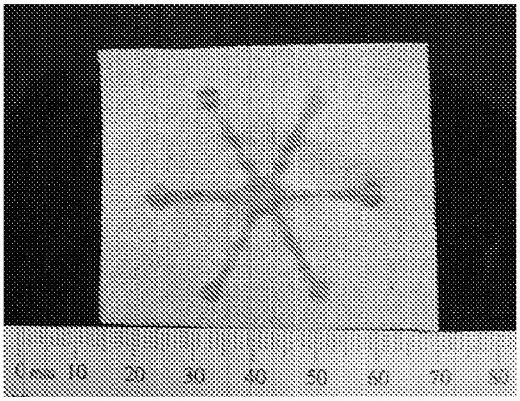
FIG. 3 shows a capillary channel pattern fabricated on two ply tissue paper according to the first embodiment of the present invention.

In a second embodiment of the invention as shown in FIG. 3, micro-channels were formed onto composites cellulosic materials. A two-ply Kleenex mainline facial tissue was treated similarly to example 1. FIG. 3 represents the liquid filled micro-channels on Kleenex two-ply tissue.

Example 3

Figure 4:
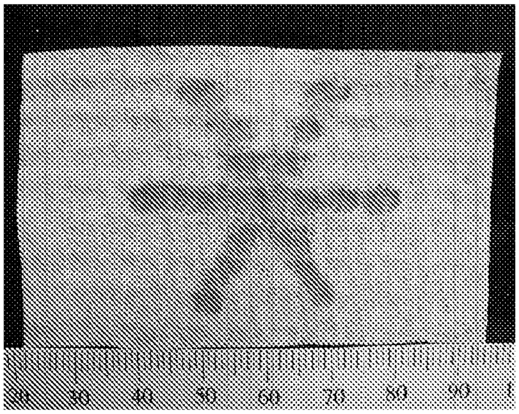
FIG. 4 shows a capillary channel pattern fabricated on a kitchen paper towel according to the first embodiment of the present invention.

In a third embodiment of the invention as shown in FIG. 4, micro-channels were formed onto a layered and molded paper basesheet. A three-layer molded paper towel (Kimberly-Clark Viva) was treated similarly to example 1. FIG. 4 represents the liquid filled micro-channels on three-layer Kimberly-Clark Viva towel.

Example 4

Figure 5:
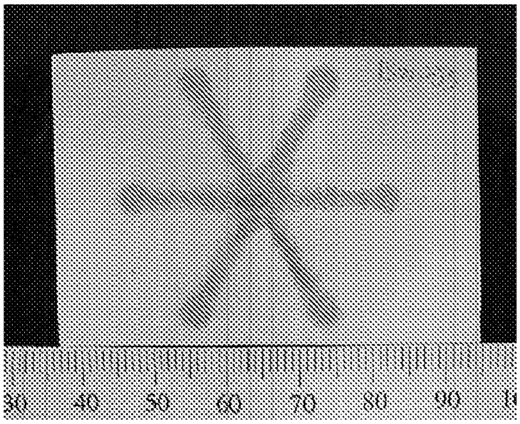
FIG. 5 shows a capillary channel pattern fabricated on photocopy paper according to the first embodiment of the present invention.

In the fourth embodiment of the invention as shown in FIG. 5, micro-channels were created on non-woven materials containing nano- and micro-fillers. Reflex copy paper (80 gsm) contains 15% calcium carbonate fillers of the particle size typically 1-2 μm. Reflex copy paper is sized and does not require hydrophobic treatment. A plasma treatment created the micro-channel pattern on to the copy paper as shown in FIG. 5.

Example 5

Figure 6:
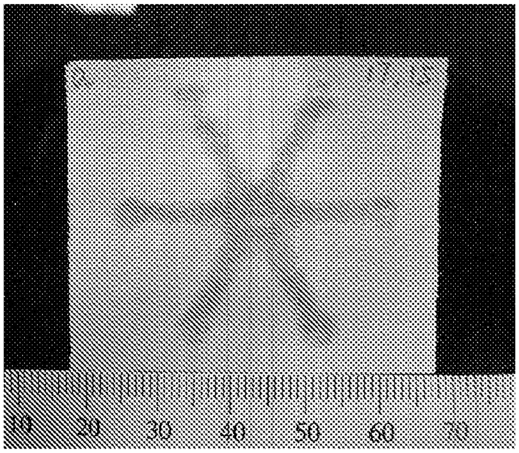
FIG. 6 shows a capillary channel pattern fabricated on news print paper according to the first embodiment of the present invention.

In the fourth embodiment of the invention as shown in FIG. 6, micro-channels were created on non-woven materials containing nano- and micro-fillers, lignocellulosic fibres and recycled paper fibres. Norstar newsprint paper (55 gsm) contains>50% recycle fibres, lignocellulosic fibres, calcium carbonate and clay fillers of the particle size typically 1-2 μm. A plasma treatment created the micro-channel pattern on the Norstar newsprinting paper.

The remaining examples illustrate a second embodiment of the present invention that utilises ink jet printing technology to define the microfluidic channels.

Example 6

Alkenyl ketene dimer (liquid AKD) was used to formulate printing fluids which were solvent-based and water-based. Any method known in the art can be selected to hydrophobize the surface/substrate. An embodiment of the invention consists of absorbing or adsorbing a solution of hydrophobic substance dissolved in a volatile solvent or suspended in emulsion form. Hydrophobic substance include, but are not restricted to, AKD, ASA, rosin, latex, silicones, fluorochemicals, polyolefin emulsions, resin and fatty acids, natural and synthetic waxes and any hydrophobic substance known in the art. Solvent-based printing fluids were formulated using solvents in which AKD can dissolve. These typically include, but are not restricted to, chloroform, dichloromethane, toluene, hexane, heptane and their mixtures. A solvent soluble dye can also be added into the printing fluid if visibility of the printed pattern is required. Water-based printing fluid can be formulated using one or a mixture of polar solvents and water. These include, but are not restricted to, acetone, alcohols and esters. AKD can be first dissolved into polar solvent or their mixture and then mix with water. The concentration of hydrophobic agents in printing fluids was 0.5%-8% v/v.

In this example digital ink jet printing method was used to print the printing fluids on paper. Microfluidic patterns were printed on Whatman #4 filter paper. Printing fluids show good penetration into the paper sheets and dry quickly. The printed patterns were subjected to a high temperature treatment to cure AKD so that it reacts with cellulose and develops strong hydrophobicity.

Figure 7:
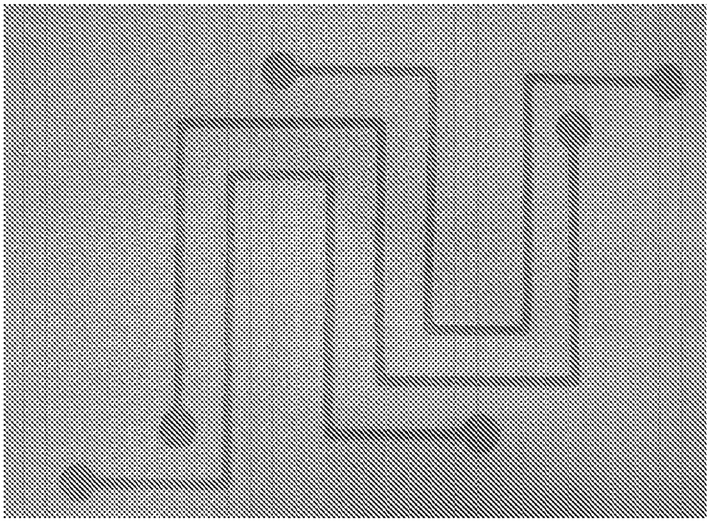
FIG. 7 shows printed microfluidic patterns fabricated according to a second embodiment of the present invention.

FIG. 7 shows a printed microfluidic patterns in which liquid penetration channels are confined by the printed hydrophobic areas.

Example 7

Figure 8:
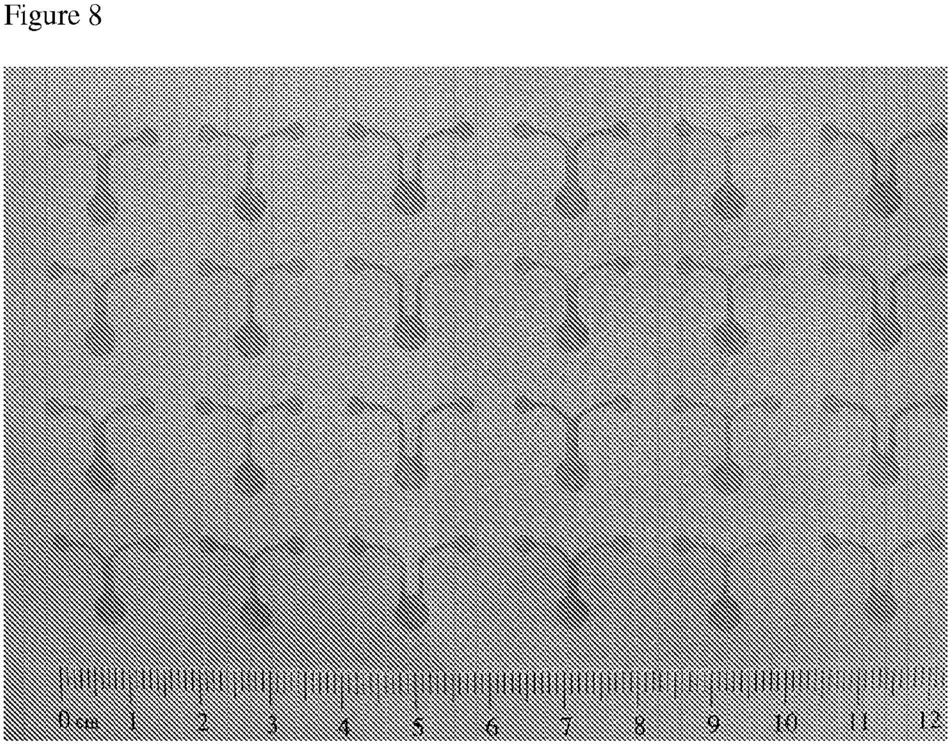
FIGS. 8 and 9 show different microfluidic patterns printed using a desktop digital ink jet printer on filter paper according to the second embodiment of the invention.
Figure 9:
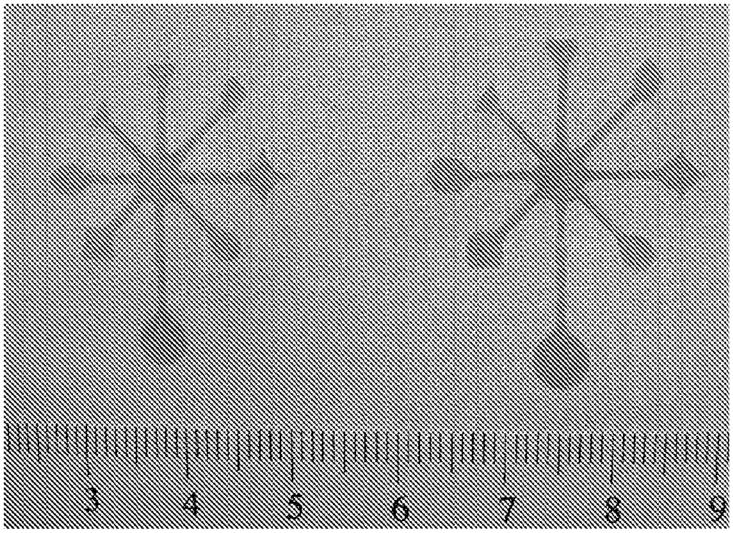

In this example as shown in FIGS. 8 and 9, the applicants show the use of printing method to fabricate microfluidic systems in a continuous manner, massive quantity, on-demand variation of patterns and very low cost.

FIG. 8 shows different microfluidic patterns printed using a desktop digital ink jet printer on a large filter paper sheet. Ink jet printing can print on A4 sheets in a continuous manner.

FIG. 8 and FIG. 9 show different microfluidic patterns can be designed and form the page-data. Digital ink jet printing can print different patterns in any desirable sequence and in any quantity required.

Example 8

Figure 10:
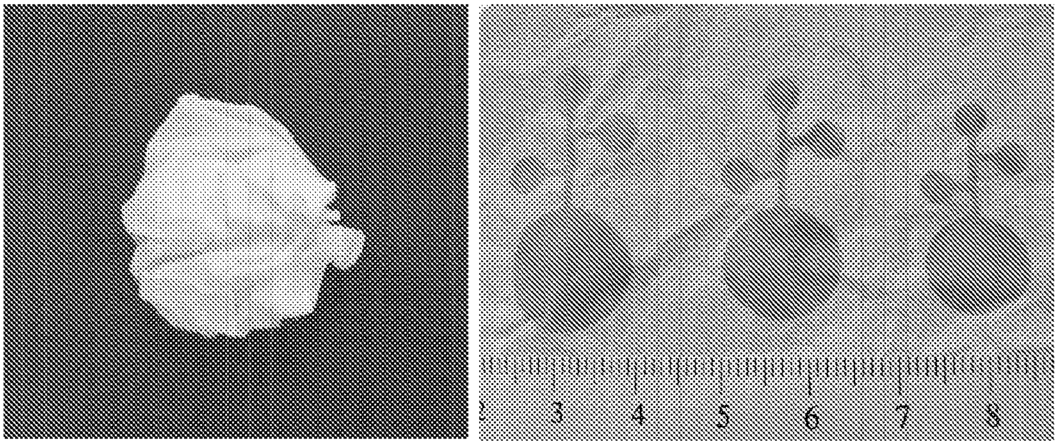
FIG. 10 shows the benching and folding resistance of the microfluidic patterns printed according to the second embodiment of the invention.

In this example as shown in FIG. 10, the applicants show that the microfluidic devices fabricated by printing of hydrophobization agents on paper are able to retain the flexibility of the papersheet and overcome the problem associated with an early design by Martinez et al. (Angew. Chem. Int. Ed. 46 (2007) 1318-1320).

FIG. 10 shows the bending and folding resistance of the printed microfluidic patterns. A printed paper microfluidic pattern was crumbled, but it still functioned well after the paper was opened up.

Example 9

Figure 11:
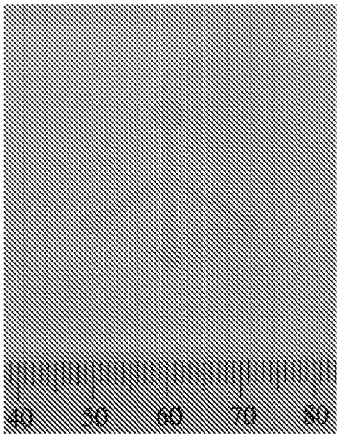
FIGS. 11 and 12 show the pattern of a microfluidic channel and an immunohistochemical staining enzyme printed according to the second embodiment of the invention.
Figure 12:
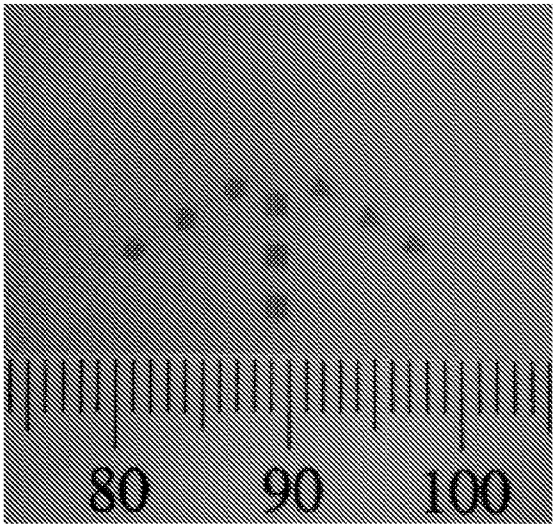

The applicants show in FIGS. 11 and 12 that printing methods can be used to fabricate devices for biomedical tests. The unique advantage of printing methods is that they can transfer several fluids onto paper or other non-woven materials to form a pattern consisting of a microfluidic system and biomedical/chemical agents for testing purposes. Modern printing methods are capable of providing accurate registration for biomedical/chemical agents to be printed inside the microfluidic systems for the designed purposes. Therefore modern printing processes can fabricate devices consisting of microfluidic channels and biomedical/chemical detection mechanisms in a single process.

FIG. 11 shows the pattern of a microfluidic channel in which an immunohistochemical staining enzyme (horseradish peroxidase) was then printed. After a colour substrate (3,3'-diaminobenzidine tetrahydrochloride) was introduced into the microfluidic system via the central sample dosing site, it penetrated into channels. A colour change was obtained which confirmed that printed immunohistochemical staining enzyme was active after printing. FIG. 12 shows the colour change after the microfluidic system was allowed to dry.

The invention claimed is:

1. A method of fabricating a flexible microfluidic device having microfluidic channels on a surface of a flexible hydrophilic substrate formed of cellulosic material, the method including the steps of:

(a) hydrophobizing the flexible hydrophilic substrate surface by absorbing or adsorbing a hydrophobic substance on or within the substrate;

(b) locating a mask defining the substrate surface, the mask having open areas defining the periphery of the microfluidic channels; and (c) applying an irradiation treatment to areas of the substrate surface exposed by the open areas of the mask, said exposed areas becoming hydrophilic to therefore form said microfluidic channels while retaining flexibility of the flexible hydrophilic substrate.

2. The method according to claim 1, wherein the surface is hydrophobized using a solution including a hydrophobic substance dissolved in a volatile solvent, the hydrophobic substance being selected from an alkyl ketene dimer (AKD), alkenyl succinic anhydride (ASA), rosin, latex, silicones, fluorochemicals, polyolefin emulsions, resin and fatty acids, natural and synthetic waxes.

3. The method according to claim 1 wherein the irradiation treatment includes plasma and corona treatments.

4. A microfluidic device, said device comprising microfluidic channels, wherein the microfluidic channels of the device are positioned on a flexible portion of a cellulosic substrate, said device fabricated by the method according to claim 1.

5. The method of claim 1 wherein the cellulosic material comprises paper, a woven cellulosic material, or a non-woven cellulosic material.

6. The method of claim 1, wherein the flexible hydrophilic substrate comprises a porous material.

7. The microfluidic device according to claim 4, wherein the surface is hydrophobized using a solution including a hydrophobic substance dissolved in a volatile solvent, the hydrophobic substance being selected from an alkyl ketene dimer (AKD), alkenyl succinic anhydride (ASA), rosin, latex, silicones, fluorochemicals, polyolefin emulsions, resin and fatty acids, natural and synthetic waxes.

8. The microfluidic device according to claim 4 wherein the irradiation treatment includes plasma and corona treatments.

9. The microfluidic device according to claim 4, wherein the cellulosic material comprises a porous material.

10. The microfluidic device according to claim 4, wherein the cellulosic material comprises paper, a woven cellulosic material, or a non-woven cellulosic material.

* * * * *